United States Patent [19]
Campbell et al.

[11] Patent Number: 5,874,589
[45] Date of Patent: Feb. 23, 1999

[54] METHODS FOR SYNTHESIZING DIVERSE COLLECTIONS OF TETRAMIC ACIDS AND DERIVATIVES THEREOF

[75] Inventors: David A. Campbell, San Mateo; Todd T. Romoff, San Jose, both of Calif.

[73] Assignee: Glaxo Wellcome, Inc., Research Triangle Park, N.C.

[21] Appl. No.: 896,799

[22] Filed: Jul. 18, 1997

[51] Int. Cl.$^6$ .................. C07D 211/40; C07D 207/00
[52] U.S. Cl. ...................... 548/540; 546/220; 548/539
[58] Field of Search ............................ 546/220; 548/539, 548/540

[56] References Cited

U.S. PATENT DOCUMENTS

| | | | |
|---|---|---|---|
| 3,299,095 | 1/1967 | Harris et al. | 548/531 |
| 3,361,626 | 1/1968 | Harris et al. | 514/425 |
| 3,752,814 | 8/1973 | Fluckiger et al. | 544/346 |
| 3,752,888 | 8/1973 | Fluckiger et al. | 514/250 |
| 3,923,790 | 12/1975 | Imanaka et al. | 540/456 |
| 3,929,790 | 12/1975 | Leimgruber et al. | 544/347 |
| 3,984,559 | 10/1976 | Weinstock | 514/343 |
| 4,522,911 | 6/1985 | Clecak et al. | 430/192 |
| 4,683,202 | 7/1987 | Mullis | 435/91.2 |
| 4,694,081 | 9/1987 | Miller et al. | 544/385 |
| 4,965,188 | 10/1990 | Mullis et al. | 435/6 |
| 5,147,875 | 9/1992 | Coates et al. | 514/259 |
| 5,164,388 | 11/1992 | De et al. | 514/235.8 |
| 5,288,514 | 2/1994 | Ellman | 435/4 |
| 5,324,483 | 6/1994 | Cody et al. | 422/131 |
| 5,475,013 | 12/1995 | Talley et al. | 514/311 |
| 5,498,732 | 3/1996 | Loffet | 549/274 |

FOREIGN PATENT DOCUMENTS

| | | | |
|---|---|---|---|
| 2 266 888 | 11/1993 | United Kingdom | C07D 207/44 |
| WO 92/00091 | 1/1992 | WIPO | A61K 37/02 |
| WO 95/12608 | 5/1995 | WIPO | C07K 1/04 |

OTHER PUBLICATIONS

Armstrong et al., 1996, Acc. Chem. Res. 29: 123–131 Multiple–component condensation stratgies for combinatorial library synthesis.

Bertho et al., 1991, Tetrahedron Ltrs. 32: 1303–1306 Amino acid flourides: Their preparation and use in peptide synthesis.

Brenner et al. (1992), Proc. Natl. Acad. Sci. USA 89:5381–5383. Encoded combinatorial chemistry.

Burger et al., 1993, J. Fluorine Chem. 65: 149–152 3,3, 3–trifluoro–2–isocyanopropionates, new versatile building blcoks for the introduction of trifluoromethyl groups into organic molecules.

Carpino et al. (1990), J. Am. Chem. Soc. 112:9651–9652 ((9–Fluorenylmethyl)oxy)carbonyl (FMOC)) amino acid fluorides.

Chaturvedi et al., 1970, J. Med. Chem. 13: 177–181 Analogs of angiotensis II. I. Solid Phase Synthesis.

Coy et al., 1988, Tetrahedron, 44: 835–841 Solid phase reductive alkylation techniques in analogue peptide bond and side chain modification.

El Marini et al., 1992, Synthesis pp. 1104–1108 Synthesis of enantiomerically pure β–and γ–amino acids from aspartic and glutamic acid derivatives.

Evans et al., 1982, J. Amer. Chem. Soc. 104: 1737–1739 Asymmetric alkylation reactions of chiral imide enolates. A practical approach to the enantioselective synthesis of α–substituted carboxylic acid derivatives.

Fontenot et al., 1991, Peptide Research, 4: 19–25 A survey of potential problems and qulaity control in peptide synthesis by the flourenylmethocvarbonyl procedure.

Giesemann et al., 1982, J. Chem. Res. (S) pp. 79 Synthesis of chiral α–isocyano esters and other base–sensitive isocyanides with oxomethylenebis–(3H–Imidazolium)Bis(methanesulphonate), a versatile dehydrating reagent.

Geysen et al., 1987, J. Immunol. Meth. 102: 259–274 Strategies for epitope analysis using peptide synthesis.

Giron–Forest et al., 1979, Analytical Profiles of Drug Substances, 8: 47–81 Bromocriptine methanesulphonate.

Gokel et al, 1971, Isonitrile Chemistry, Ugi, I. ed., Academic Press, NY pp. 145–199 Four–component condensations and related reactions.

Gordon et al., 1995, Bioorganic & Medicinal Chemistry Letters, 5: 47–50 Reductive alkylation on a solid phase: Synthesis of a piperazinedione combinatorial library.

Hasumi et al, 1993, J. Antibiotics 46: 1782–1787 Lateritin, a new inhibitor of acyl–CoA: cholesterol acyltransferase produced by Gibberella.

Ho et al., 1993, Peptide Research, 6: 10–12 An improved low racemization solid–phase method for the synthesis of reduced dipeptide (YCH2NH) Bond Isosteres.

Horwell et al. (1993), Bioorganic & Medicinal Chemistry Letters, 3(5):799–802 The Design of a dipeptide library for screening at peptide receptor sites.

Hwang et al., 1983, Biochemistry 22: 4756–4763 Specific receptor sites for 1–O–Alkyl–2–O–acetyl–sn–glycero–3–phosphocholine (platelet activating factor) on rabbit platelet and guinea pig smooth muscle membranes.

Jung and Beck–Sickinger (1992), Angewandte Chemie 31(4):367–486 Multiple peptide synthesis methods and their applications.

Keating et al., 1996, J. Am. Chem. Soc. 118:2574–2583 Postcondensation modifications of Ugi four–condensation products: 1–isocyanocyclohexene as a convertible isocyanide.

(List continued on next page.)

Primary Examiner—John Kight
Assistant Examiner—Garth M. Dahlen
Attorney, Agent, or Firm—Lauren L. Stevens

[57] ABSTRACT

Disclosed are methods for synthesizing very large collections of diverse diverse tetramic acids, tetronic acids, pentamic acids, pentonic acids, and derivatives thereof and synthetic compound libraries comprising compounds prepared by such methods.

7 Claims, No Drawings

OTHER PUBLICATIONS

Kim et al. (1992), Tetrahedron Asymmetry, 3: 1421–1430 Polymer attached cyclic dipeptides as catalysts for enantioselective cyanohydrin formation.

Kucharczyk et al., 1993, J. Med. Chem., 36: 1654–1661 Tetrapeptide tachykinin antagonists: Synthesis and modulationof the physicochemical and pharmacological properties of a new series of partially cyclic analogs.

Leznoff (1978), Account of Chemical Research, pp. 327–333 The use of insoluble polymer supports in general organic synthesis.

Palom et al., 1993, Tetrahedron Letters, 34: 2195–2198 An acid–labile linker for solid–phase oligoribonucleotide synthesis using Fmoc group for 5'–hydroxyl protection.

Rajappa et al., 1993,Advances in heterocyclic chemistry 57:187–289 Piperazine–2,5–diones and related lactim ethers.

Sammes et al., 1975, Chem. Org. Naturst., 32: 51–118 Naturally occuring 2,5–dioxopiperazines and related compounds.

Scott et al., 1995, Molecular Diversity 1(2): 125–134 Solid phase organic synthesis (SPOS):a novel route to diketopiperazines and diketomorpholines.

Shen et al., Feb. 1985, Proc. Natl. Acad. Sci. USA. 82: 672–676 Characerization of a platelet–activating factor receptor antagonist isolated from haifenteng (piper futokadsura): Specific inhibition of in vitro and in vivo platelet–activating factor–induced effects.

Shih et al., 1990, J. Am. Chem. Soc., 112: 9652–9654 Biosynthesis of 3,6–Dideoxyhexoses: Strereochemical Analysis of the Deprotonation Catalyzed by the Pyriodxamine 5'–Phosphate Dependent Enzyme CDP–4–keto–6–deoxy–D–glucose–3–dehydrase Isolated from Yersinia Pseudotuberculosis.

Shimazaki et al., 1987, Chem Parm. Bull., 35: 3527–3530 Diketopiperazine derivatives, A new series of platelet–activating factor inhibitors.

Shimazaki et al., 1987, J. Med. Chem. 30: 1706–1709 Diketopiperazines as a new class of platelet–activating factor inhibitors.

Shiosaki et al., 1990, *Peptides: Chemistry Structure and Biology* ESCOM Science Publishers B.V., The Netherlands, pp. 978–980 Toward development of peptidomimetics: Diketopiperazine templates for the Trp–Met segment of CCK–4.

Shiosaki et al., 1993,Bioorganic & Medicinal Chemistry Letters, 3: 855–860 Toward development of peptidomimetics: Diketopiperazine templates for the Trp–met segment of CCK–4.

Williams et al., 1988, Chem Rev., 88: 511–540 Bicyclomycin: Synthetic, Mechanistic, and Biological Studies.

Winitz et al., 1956, J. Amer. Chem. Soc. 78:2423–2430 Studies on diastereoisomeric α–amino acids and corresponding α–hydroxy acids. VII. Influence of β–configuration on enzymic susceptibility.

Zuckermann et al., 1992, J. Am. Chem. Soc. 114: 10646–10647 Efficient method for the preparation of peptoids [oligo(N–substituted glycines)] by submonomer solid–phase synthesis.

Jouin, P. et al, J. Chem. Soc. Perkin Trans. I, 1987, p. 1177.

METHODS FOR SYNTHESIZING DIVERSE COLLECTIONS OF TETRAMIC ACIDS AND DERIVATIVES THEREOF

BACKGROUND OF THE INVENTION

1. Field of the Invention

This invention is directed to methods for synthesizing very large collections of diverse tetramic acids (i.e., 2,4-pyrrolidinediones) and derivatives thereof, including tetronic acids, thiotetronic acids, pentamic acids, pentonic acids, and thiopentonic acids. This invention is further directed to methods for identifying and isolating tetramic acid compounds and derivatives thereof with useful and diverse activities from such collections.

2. State of the Art

Compounds having biological activity can be identified by screening diverse collections of compounds (i.e., libraries of compounds) produced through either molecular biological or synthetic chemical techniques. Such screening methods include methods wherein each member of the library is tagged with a unique identifier tag to facilitate identification of compounds having biological activity or where the library comprises a plurality of compounds synthesized at specific locations on the surface of a solid substrate wherein a receptor is appropriately labeled to identify binding to the compound, e.g., fluorescent or radioactive labels. Correlation of the labeled receptor bound to the substrate with its location on the substrate identifies the binding compound.

Central to these methods is the screening of a multiplicity of compounds in the library and the ability to identify the structures of the compounds which have a requisite biological activity. Preferably, in order to facilitate synthesis and identification, the compounds in the library are typically formed on solid supports wherein the compound is covalently attached to the support via a cleavable or non-cleavable linking arm. In this regard, libraries of diverse compounds are prepared and then screened to identify "lead compounds" having good binding affinity to the receptor.

Pharmaceutical drug discovery relies heavily on studies of structure-activity relationships wherein the structure of "lead compounds" is typically altered to determine the effect of the alteration on activity. Alteration of the structure of the lead compounds permits evaluation of the effect of the structural alteration on activity. Thus libraries of compounds derived from a lead compound can be created by including derivatives of the lead compound and repeating the screening procedures.

Ideally, the compounds are synthesized in situ on the solid support so that the support can be tagged to identify the synthetic steps employed and/or the derivative incorporated onto the support. However, relatively simple synthetic methods to produce a diverse collection of such derivatives on the supports are often not available.

One particular class of compounds which would be useful for inclusion in screening libraries are tetramic acids compounds. 3-Acyl-2,4-pyrrolidinediones (acyltetramic acids) are a class of natural products that have attracted significant attention over the years as a result of their biological activities and the synthetic challenges presented by their complex structures. Representative examples of this structural class include streptolydigin, tirandamycin A, BU2313A and BU2313B which are natural products extracted from fungi that exhibit potent antibacterial activities. Streptolydigin and tirandamycin exhibit potent activity against Gram-positive organisms by inhibiting terminal DNA transferase and bacterial RNA polymerase enzymes. BU2313A and BU2313B are broad-spectrum antibiotics effective against both Gram-positive and Gram-negative anaerobic bacteria as well as some aerobic bacteria including Streptococci. Tirandamycin and the BU2313 compounds have exhibited efficacy in mouse protection tests, and tirandamycin in a mouse abscess model for *Bacteroides fragilis*.

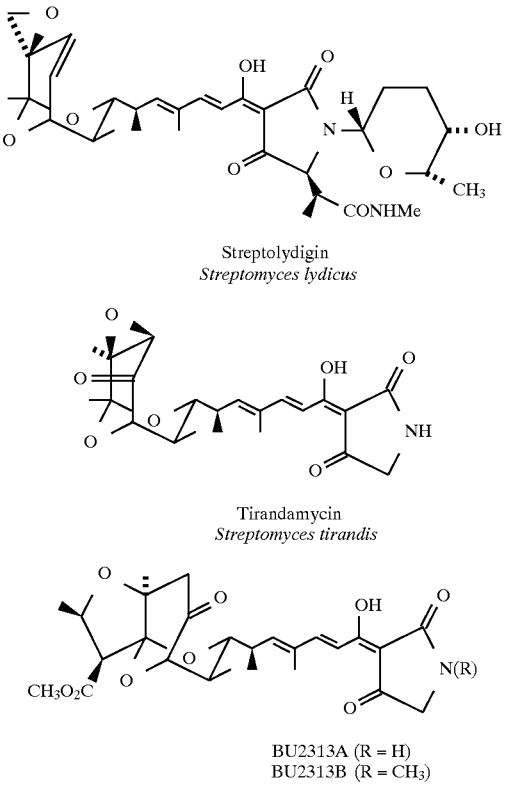

Streptolydigin
*Streptomyces lydicus*

Tirandamycin
*Streptomyces tirandis*

BU2313A (R = H)
BU2313B (R = CH₃)

Although the complicated polycyclic side chains of the above antibiotics may be required for inhibition of RNA polymerase and DNA transferase, the 3-acyl-2,4-pyrrolidinedione unit itself offers significant potential as a drug scaffold. With a pKa of 5, the ability to chelate metals, and the two ketone units, acyltetramic acids possess a number of potential binding modes with biological targets.

Tetramic acids and derivatives thereof are also valuable chiral starting materials for the synthesis of other natural and unnatural products.

A variety of solution phase techniques have been developed to prepare tetramic acids. For example, it is known to condense activated N-protected alpha-amino acids with Meldrum's acid to yield the corresponding 1-hydroxyalkylidene Meldrum's acid. Upon heating in solution acetone and $CO_2$ are eliminated to form N-protected 5-substituted tetramic acids. See Jouin et al. (1987) *J. Chem. Soc. Perkin Trans. I* 1177. Alternatively, alpha-amino acid esters can be reacted with malonic acid ester chlorides to yield the corresponding N-(alkoxycarbonylacetyl)-alpha amino acid esters. The latter are cyclized to the 3-alkoxycarbonyl tetramic acids. See Mulholland et al. (1972) *J. Chem. Soc. Perkin Trans. I* 2121. See, also, U.S. Pat. No. 5,008,402, U.S. Pat. No. 5,534,540, U.S. Pat. No. 5,468,774, U.S. Pat. No. 4,996,227, and U.S. Pat. No. 5,498,732.

However, the incorporation of a multiplicity of tetramic acid derivatives on solid supports is not previously known.

The ability to synthesize a multiplicity of tetramic acid derivatives on a solid support or on different solid supports would enhance the structural variation of a library and provide important structure-activity information.

SUMMARY OF THE INVENTION

This invention is directed to general synthetic methods for preparing tetramic acids and derivatives thereof, including thiotetronic acids, pentamic acids, pentonic acids, and thiopentonic acids, which methods can be employed in conjunction with known stochastic methods for preparing libraries of compounds comprising one or more tetramic acid or related groups. In one embodiment, the compounds can be further derivatized thereby elaborating their structure.

Accordingly, in one of its method aspects, this invention is directed to a method for synthesizing a tetramic acid or pentamic acid group or derivative thereof which method comprises:

(a) providing an amine component immobilized on a solid support;

(b) contacting the amine component with a β-keto ester equivalent to yield a β-keto amide; and (c) treating the β-keto amide under conditions suitable for the cyclization and concomitant release of the compound from the solid support.

The amine component may comprise a primary amino group having the formula: R-NH$_2$, wherein R is selected from the group consisting of alkyl, amino, aryl, heteroaryl, and arylalkyl or salts thereof. According to the latter embodiment, R can also be hydrogen. More preferably, the amine component will have the formula:

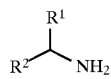

wherein R$^1$ and R$^2$ are independently selected from the groups consisting of hydrogen, alkyl, aryl, heteroaryl, carboxyl, carboxyalkyl, and arylalkyl. More preferably, the amine component will comprise an alpha- (i.e., to produce a tetramic acid) or beta-amino acid (i.e., to produce a pentamic acid). In a particularly preferred embodiment, the amine group of the amine component will be alkylated.

Preferably, the β-keto ester equivalent will comprise an acyl Meldrum's acid, a lower alkyl ester of a β-keto carboxylic acid, or an acyl chloride of a β-keto carboxylic acid. Most preferably, the β-keto ester equivalent will comprise an acyl Meldrum's acid.

Other embodiments of the invention are drawn to the synthesis of analogs of tetramic acids, such as thiotetronic acids, pentamic acids, pentonic acids, and thiopentonic acids and derivatives thereof. According to this embodiment, a hydroxyl or thiol component is contacted with a β-keto ester to yield a second β-keto ester. As in the synthesis of tetramic acids, Diekmann cyclization and concomitant release from the support yields the desired compound. If the hydroxyl component comprises an α-hydroxy acid, tetronic acids are formed. Likewise, if β-hydroxy acids are used, pentonic acids are produced. If an α-mercapto acid is used, thiotetronic acids result. Likewise, if a β-mercapto acid is used, thiopentonic acids result.

In another of its method aspects, this invention is directed to a method for preparing a library of tetramic acids, pentamic acids or derivatives thereof, which library is synthesized in a process comprising:

a) apportioning the supports comprising a covalently bound amine component, preferably, an alpha- or beta-amino acid, among a plurality of reaction vessels, b) contacting the amine component with a β-keto ester equivalent to yield a β-keto amide; and c) treating the β-keto amide under conditions suitable for the cyclization and concomitant release of the tetramic acid group from the solid support.

In a particularly preferred embodiment, step a) of the method further comprises the step of reductively alkylating the covalently bound amine component.

DETAILED DESCRIPTION OF THE INVENTION

I. Terminology

Prior to discussing this invention in further detail, the following terms will first be defined:

"Alkoxy" refers to the group alkyl-O-.

"Alkyl" refers to a cyclic, branched, or straight chain chemical group containing only carbon and hydrogen, such as methyl, heptyl, —(CH$_2$)$_2$—, and adamantyl. Alkyl groups can either be unsubstituted or substituted with one or more substituents, e.g., halogen, alkoxy, acyloxy, amino, aryl, hydroxyl, mercapto, carboxy, benzyloxy, phenyl, benzyl, or other functionality which may be suitably blocked, if necessary for purposes of the invention, with a protecting group. Typically, alkyl groups will comprise 1 to 12 carbon atoms, preferably 1 to 10, and more preferably 1 to 8 carbon atoms.

"Amino" or "amine group" refers to the group —NR'R", where R' and R" are independently selected from the group consisting of hydrogen, alkyl, substituted alkyl, aryl, substituted aryl, aryl alkyl, substituted aryl alkyl, heteroaryl, and substituted heteroaryl. In a primary amino group, both R' and R" are hydrogen, whereas in a secondary amino group, either, but not both, R' or R" is hydrogen.

An "α-amino acid" consists of a carbon atom, called the α-carbon, to which is bonded an amino group and a carboxyl group. Typically, this α-carbon atom is also bonded to a hydrogen atom and a distinctive group referred to as a "side chain." The hydrogen atom may also be replaced with a group such as alkyl, substituted alkyl, aryl, substituted aryl, heteroaryl, and other groups. The side chains of naturally occurring amino acids are well known in the art and include, for example, hydrogen (as in glycine), alkyl (as in alanine (methyl), valine (isopropyl), leucine (sec-butyl), isoleucine (iso-butyl), and proline (—(CH$_2$)$_3$—)), substituted alkyl (as in serine (hydroxymethyl), cysteine (thiomethyl), aspartic acid (carboxymethyl), asparagine, arginine, glutamine, glutamic acid, and lysine), aryl alkyl (as in phenylalanine, histidine, and tryptophan), substituted aryl alkyl (as in tyrosine and thyroxine), and heteroaryl (as in histidine). See, e.g., Harper et al. (1977) *Review of Physiological Chemistry* 16th Ed., Lange Medical Publications, pp. 21–24.

In addition to naturally occurring side chains, the amino acids used in the present invention may possess synthetic side chains. A "synthetic side chain" is any side chain not found in a naturally occurring amino acid. For example, a synthetic side chain can be an isostere of the side chain of a naturally occurring amino acid. Naturally occurring and synthetic side chains may contain reactive functionalities, such as hydroxyl, mercapto, and carboxy groups. One skilled in the art will appreciate that these groups may have to be protected to carry out the desired reaction scheme. As stated above, the hydrogen at the α-carbon can also be replaced with other groups; those of skill in the art recognize the medicinal importance of α-methyl amino acids and other α-, α-disubstituted amino acids.

"Aryl" or "Ar" refers to an aromatic carbocyclic group having a single ring (e.g., phenyl) or multiple condensed rings (e.g., naphthyl or anthryl), which can optionally be unsubstituted or substituted with amino, hydroxyl, lower alkyl, alkoxy, aryloxy, chloro, halo, mercapto, aryl, and other substituents. Preferred aryl groups include phenyl, 1-naphthyl, 2-naphthyl, biphenyl, phenylcarboxylphenyl (i.e., derived from benzophenone), and the like.

"Aryloxy" refers to the group aryl-O- or heteroaryl-O-.

"Arylalkyl" refers to the groups R'—Ar and R-HetAr, where Ar is an aryl group, HetAr is a heteroaryl group, and R' is straight-chain or branched-chain aliphatic group. Examples of arylalkyl groups include benzyl and furfuryl.

"Carboxy" or "carboxyl" refers to the group —R'(COOH) where R' is alkyl, substituted alkyl, aryl, substituted aryl, aryl alkyl, substituted aryl alkyl, heterocyclic, heteroaryl, or substituted heteroaryl.

"Carboxyalkyl" refers to the group —(CO)—R' where R' is alkyl or substituted alkyl.

"Carboxyaryl" refers to the group —(CO)—R' where R' is aryl, heteroaryl, or substutited aryl or heteroaryl.

"Chemical library" or "array" is an intentionally created collection of differing molecules which can be prepared either synthetically or biosynthetically and screened for biological activity in a variety of different formats (e.g., libraries of soluble molecules; and libraries of compounds tethered to resin beads, silica chips, or other solid supports). The term is also intended to refer to an intentionally created collection of stereoisomers.

"Combinatorial synthesis strategy" or "combinatorial chemistry" refers to an ordered strategy for the parallel synthesis of diverse compounds by sequential addition of reagents which leads to the generation of large chemical libraries. Thus, combinatorial chemistry refers to the systematic and repetitive, covalent connection of a set of different "building blocks" of varying structures to each other to yield large arrays of diverse molecular entities.

"Heteroaryl" or "HetAr" refers to a monovalent unsaturated aromatic carbocyclic group having a single ring (e.g., pyridyl or furyl) or multiple condensed rings (e.g., indolizinyl or benzothienyl) and having at least one hetero atom, such as N, O, or S, within the ring, which can optionally be unsubstituted or substituted with amino, hydroxyl, alkyl, alkoxy, halo, mercapto, and other substituents.

"Identifier tag" denotes a physical attribute that provides a means whereby one can identify a chemical reaction. The identifier tag serves to record a step in a series of reactions used in the synthesis of a chemical library. The identifier tag may have any recognizable feature, including for example: a microscopically or otherwise distinguishable shape, size, mass, color, optical density, etc.; a differential absorbance or emission of light; chemical reactivity; magnetic or electronic properties; or any other distinctive mark capable of encoding the required information, and decipherable at the level of one (or a few) molecules. A preferred example of such an identifier tag is an oligonucleotide, because the nucleotide sequence of an oligonucleotide is a robust form of encoded information. Identifier tags can be coupled to the solid support. Alternatively, the "identifier tag" can be coupled directly to the compound being synthesized, whether or not a solid support is used in the synthesis. In the latter embodiment, the identifier tag can conceptually be viewed as also serving as the "support" for synthesis.

"Linker" refers to a molecule or group of molecules attached to a solid support and spacing a synthesized compound from the solid support, such as for exposure/binding to a receptor.

"Pentamic acid" refers to the basic ring structure:

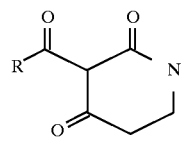

wherein the nitrogen and carbon atoms may bear a variety of substituents as described hereinbelow.

"Pentonic acid" refers to the basic ring structure:

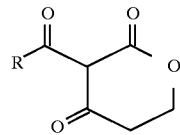

wherein the carbon atoms may bear a variety of substituents as described hereinbelow.

"Protecting group" refers to a chemical group that exhibits the following characteristics: (1) reacts selectively with the desired functionality in good yield to give a derivative that is stable to the projected reactions for which protection is desired; 2) can be selectively removed from the derivatized solid support to yield the desired functionality; and 3) is removable in good yield by reagents compatible with the other functional group(s) generated in such projected reactions. Examples of protecting groups can be found in Greene et al. (1991) *Protective Groups in Organic Synthesis*, 2nd Ed. (John Wiley & Sons, Inc., New York). Preferred protecting groups include photolabile protecting groups (such as methylnitropiperonyloxycarbonyl (Menpoc), methylnitropiperonyl (Menp), nitroveratryl (Nv), nitroveratryloxycarbonyl (Nvoc), or nitroveratryloxymethyl ether (Nvom)); acid-labile protecting group (such as Boc or DMT); base-labile protecting groups (such as Fmoc, Fm, phosphonioethoxycarbonyl (Peoc, see Kunz (1976) *Chem. Ber.* 109:2670); groups which may be removed under neutral conditions (e.g., metal ion-assisted hydrolysis ), such as DBMB (see Chattopadhyaya et al. (1979) *J.C.S. Chem. Comm.* 987–990), allyl or alloc (see, e.g., Greene and Wuts, "Protective Groups in Organic Synthesis", 2nd Ed., John Wiley & Sons, Inc., New York, N.Y. (1991), 2-haloethyl (see Kunz and Buchholz (1981) *Angew. Chem. Int. Ed. Engl.* 20:894), and groups which may be removed using fluoride ion, such as 2-(trimethylsilyl)ethoxymethyl (SEM), 2-(trimethylsilyl)ethyloxycarbonyl (Teoc) or 2-(trimethylsilyl)ethyl (Te) (see, e.g., Lipshutz et al. (1980) *Tetrahedron Lett.* 21:3343–3346)); and groups which may be removed under mild reducing conditions (e.g., with sodium borohydride or hydrazine), such as Lev. Id. at 30–31, 97, and 112. Particularly preferred protecting groups include Fmoc, Fm, Menpoc, Nvoc, Nv, Boc, CBZ, allyl, alloc, Npeoc (4-nitrophenethyloxycarbonyl) and Npeom (4-nitrophenethyloxy-methyloxy).

"Solid support" or "support" refers to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. The solid support is alternatively referred to herein as a support.

"Stereoisomer" refers to a chemical compound having the same molecular weight, chemical composition, and constitution as another, but with the atoms grouped differently. That is, certain identical chemical moieties are at different orientations in space and, therefore, when pure, has the ability to rotate the plane of polarized light. However, some pure stereoisomers may have an optical rotation that is so slight that it is undetectable with present instrumentation. The compounds of the instant invention may have one or more asymmetrical carbon atoms and therefore include various stereoisomers. All stereoisomers are included within the scope of the invention and within the scope of the term "tetramic acid".

"Tetramic acid" refers to the basic ring structure:

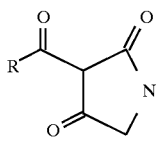

wherein the nitrogen and carbon atoms may bear a variety of substituents as described hereinbelow.

"Tetronic acid" refers to the basic ring structure:

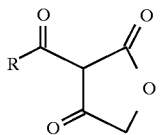

wherein the carbon atoms may bear a variety of substituents as described hereinbelow.

"Thiopentonic acid" refers to the basic ring structure:

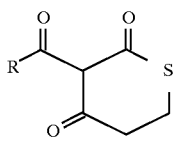

wherein the carbon atoms may bear a variety of substituents and the sulfur may be alkylated, oxidized and the like as described hereinbelow.

"Thiotetronic acid" refers to the basic ring structure:

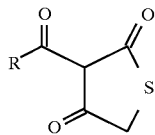

wherein the carbon atoms may bear a variety of substituents and the sulfur may be alkylated, oxidized and the like as described hereinbelow.

Isolation and purification of the compounds and intermediates described herein can be effected, if desired, by any suitable separation or purification procedure such as, for example, filtration, extraction, crystallization, column chromatography, thin-layer chromatography, thick-layer (preparative) chromatography, distillation, or a combination of these procedures. Specific illustrations of suitable separation and isolation procedures can be had by references to the examples hereinbelow. However, other equivalent separation or isolation procedures can, of course, also be used.

Abbreviations: The following abbreviations are intended to have the following meanings:

BOC=t-butyloxycarbonyl

BOP=benzotriazol-1-yloxytris(dimethylamino) phosphonium hexafluorophosphate

DCC=dicyclohexylcarbodiimide

Ddz=dimethoxydimethylbenzyloxy

DIC=diisopropylcarbodiimide

DCM=dichloromethane

DIAD=diisopropyl azodicarboxylate

DMAP=4-dimethylaminopyridine

DMT=dimethoxytrityl

Fmoc fluorenylmethyloxycarbonyl

Fmoc-Cl=fluorenylmethyloxycarbonyl chloride

HBTU=2-(1H-benzotriazol-1-yl)-1,1,3,3-tetramethyluronium hexafluorophosphate

HOBt=1-hydroxybenzotriazole

Menpoc=methylnitropiperonyloxycarbonyl

Menp=methylnitropiperonyl

Nv=nitroveratryl

Nvoc=6-nitroveratryloxycarbonyl and other photoremovable groups

OPfp=pentafluorophenyloxy

OSu=N-succinimidyloxy (also known as NHS)

PG=protective group

PPh$_3$=triphenyl phosphine

TFA=trifluoroacetic acid

II. Overview

The present invention, in one aspect, includes a highly efficient and versatile method of synthesizing and screening, preferably in parallel and simultaneous fashion, large numbers of tetramic acids or derivatives thereof. Thus, according to one aspect, the present invention provides a synthesis method for tetramic acids in which variable substituent groups are attached to a common central structure using the procedure shown below:

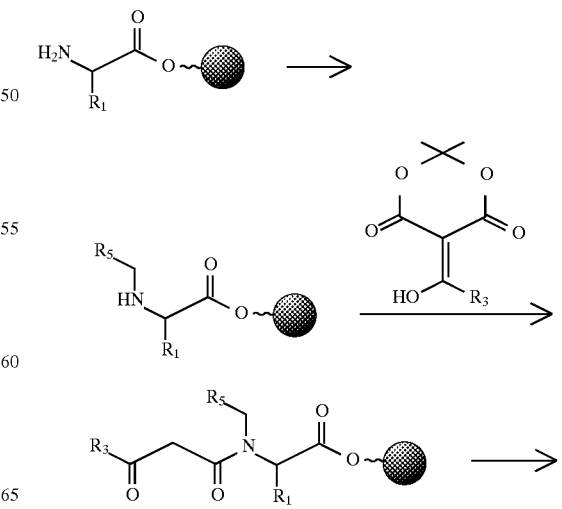

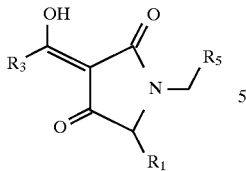

wherein $R_1$ is derived from the amine component, $R_5$ results from the alkylation of the amine component, and $R_3$ is derived from the beta-keto ester equivalent.

If the amine component comprises a beta-amino acid (or alkylated beta-amino acid), pentamic acids (i.e., 3-acyl-2,4-piperidinediones) can be prepared:

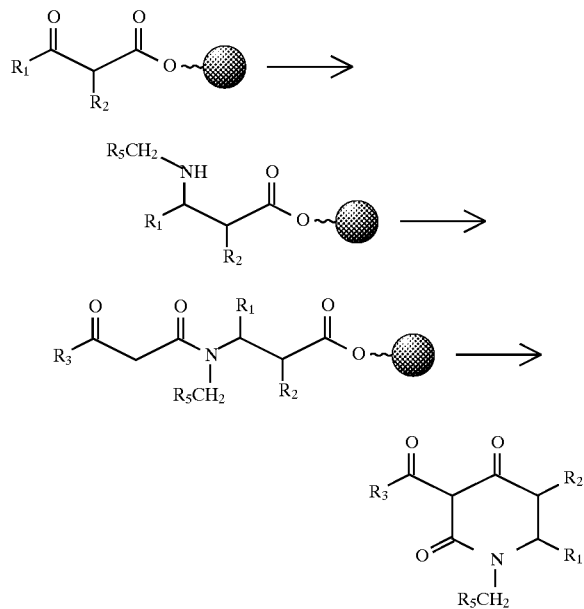

wherein $R_1$, $R_2$ and $R_5$ are derived from the amine component, and $R_3$ is derived from the beta-keto ester equivalent.

Alternatively, if a beta-hydroxy acid is used as the hydroxyl component, tetronic acids can be prepared:

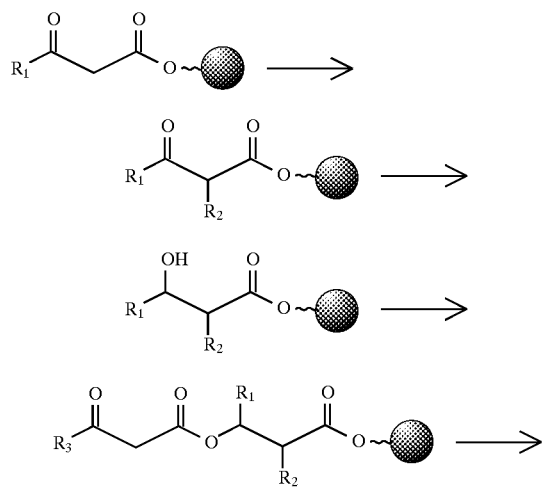

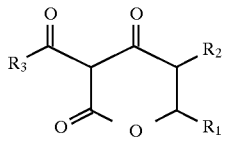

wherein $R_1$ and $R_2$ are derived from the hydroxyl component and $R_3$ is derived from the beta-keto ester equivalent. Likewise, if the hydroxyl component comprises an alpha-hydroxy acid, tetronic acids result.

The use of structures of these kinds for certain multiple simultaneous reactions is known in the art, and its application to the present invention will become apparent from the description which follows.

III. The Components

A. The Solid Support

1. Nature of the Support

Typically, the libraries or arrays of the invention are initially composed of a collection of "solid supports". Such solid supports may be of any shape, although they preferably will be roughly spherical. The supports need not necessarily be homogenous in size, shape or composition; although the supports usually and preferably will be uniform. In some embodiments, supports that are very uniform in size may be particularly preferred. In another embodiment, two or more distinctly different populations of solid supports may be used for certain purposes.

"Solid support" embraces a particle with appropriate sites for compound synthesis and, in some embodiments, tag attachment and/or synthesis. Solid supports may consist of many materials, limited primarily by capacity for derivatization to attach any of a number of chemically reactive groups and compatibility with the synthetic chemistry used to produce the array and, in some embodiments the methods used for tag attachment and/or synthesis. Suitable support materials typically will be the type of material commonly used in peptide and polymer synthesis and include glass, latex, heavily cross-linked polystyrene or similar polymers, gold or other colloidal metal particles, and other materials known to those skilled in the art. Except as otherwise noted, the chemically reactive groups with which such solid supports may be derivatized are those commonly used for solid phase synthesis of the polymer and thus will be well known to those skilled in the art, i.e., carboxyls, amines and hydroxyls.

To improve washing efficiencies, one can employ nonporous supports or other solid supports less porous than typical peptide synthesis supports; however, for certain applications of the invention, quite porous beads, resins, or other supports work well and are often preferable. A preferred support is glass, as described in U.S. Pat. No. 5,143,854, supra. Another preferred solid support is resin, such as the beads described in co-pending U.S. patent application Ser. No. 07/946,239, filed Sep. 16, 1992, supra. In general, the bead size is in the range of 1 nm to 100 µm, but a more massive solid support of up to 1 mm in size may sometimes be used. Particularly preferred resins include Merrifield resin, preferably pre-loaded with an amino acid ester, hydroxymethyl polystyrene resins; ArgoGel (available from Argonaut, S. San Francisco, Calif.); Sasrin resin (a polystyrene resin available from Bachem Bioscience, Switzerland); and TentaGel S AC, TentaGel PHB, or TentaGel S $NH_2$ resin (polystyrene-polyethylene glycol copolymer resins available from Rappe Polymere, Tubingen, Germany). Other preferred supports are commercially available and described by Novabiochem, La Jolla, Calif.

Another preferred solid support comprises a "soluble" polymer support. Typically, polyethylene glycol, polyvinylalcohol, polyvinylalcohol co-polymerized with polyvinyl pyrrolidine or derivatives thereof is used as the soluble support. See Janda and Hyunsoo (1996) *Methods Enzymol.* 267:234–247; Gravert and Janda (1997) *Chemical Reviews* 97:489–509; and Janda and Hyunsoo, PCT publication No. WO 96/03418.

2. Linkers

When bound to a solid support, the tetramic acid precursors, e.g., the amine component or the β-keto amide, are usually attached by means of one or more molecular linkers. The linker molecules preferably have lengths sufficient to allow the compounds to which they are bound to interact freely with any molecules exposed to the solid support surface, such as synthetic reagents or receptors which are an object of study. The linker molecule, prior to attachment, has an appropriate functional group at each end, one group appropriate for attachment to the support and the other group appropriate for attachment to the compound being prepared.

One can, of course, incorporate a wide variety of linkers, depending upon the application and the effect desired. For instance, one can select linkers that impart hydrophobicity, hydrophilicity, or steric bulk to achieve desired effects on properties such as coupling or binding efficiency. In one aspect of the invention, branched linkers, i.e., linkers with bulky side chains such as the linker, Fmoc-Thr(tBu), are used to provide rigidity to or to control spacing of the molecules on the solid support in a library. In some embodiments, cleavable linkers will be used to facilitate an assay or detection step as discussed more fully below.

3. Immobilization

The choice of functionality used for binding a molecule to the solid support will depend on the nature of the compound to be synthesized and the type of solid support. Conditions for coupling monomers and polymers to solid supports through a wide variety of functional groups are known in the art. See, e.g., U.S. Pat. No. 4,542,102; U.S. Pat. No. 4,282,287; Merrifield, "Solid Phase Peptide Synthesis," *J. Am. Chem. Soc.,* (1963) 85:2149–2154; Geysen et al., "Strategies for Epitope Analysis Using Peptide Synthesis," *J. Imm. Meth.,* (1987) 102:259–274; Pirrung et al., U.S. Pat. No. 5,143,854; and Fodor et al., "Light-Directed Spatially-Addressable Parallel Chemical Synthesis," *Science* (1991) 251:767–773, each of which is incorporated herein by reference.

B. The Amine Component

According to the present invention, an amine component is coupled to a β-keto ester equivalent to yield a β-keto amide which can then be cyclized with concomitant cleavage of the resulting tetramic acid from the solid support. The amine component typically will be attached to a solid support and thus, should include a functionality which can covalently bind the molecule to the solid support (e.g., an activated carbonyl, acyl halide, ester, amide, thioester, or activated hydroxyl) as well as the amino group or a protected derivative thereof.

Typically the amine component will comprise a primary amine having the formula: R-NH$_2$, wherein R is selected from the group consisting of hydrogen (i.e., an amine salt as a further valence is necessary to attach the amine component to the solid support), alkyl, amino, aryl, heteroaryl, and arylalkyl or salts thereof. More preferably, the amine component will have the formula:

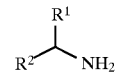

wherein $R^1$ and $R^2$ are independently selected from the groups consisting of hydrogen, alkyl, aryl, heteroaryl, carboxyl, carboxyalkyl, carboxyaryl, and arylalkyl. The amine component, if not commercially available, can be prepared by standard chemical procedures.

In a preferred embodiment, the amine component will comprise an amino acid, and more preferably, an amino acid bearing a substituent on the alpha carbon. The amino acids finding utility in the present invention include the twenty naturally occurring α-amino acids, in either their D- or L-enantiomeric forms. Unnatural amino acids such as α, α-disubstituted amino acids, N-alkyl amino acids, lactic acid, and other unconventional amino acids are also suitable components. Examples of unconventional amino acids include, but are not limited to: 4-hydroxyproline, O-phosphoserine, 3-methylhistidine, 5-hydroxylysine, and other similar amino acids. Since peptides are composed of amino acid subunits, one of skill in the art will appreciate that peptides can also serve as amine components.

Preferably, the amino group of the amine component is alkylated.

If the amine component possesses reactive sites other than the amino group, it may be necessary to protect them during the synthesis. Suitable protecting groups include acid-labile, base-labile, photoremovable, or removable under neutral conditions. See, e.g., Green, *Protecting Groups in Organic Synthesis,* Wiley 1985, pp. 218–288, which is incorporated herein by reference. The choice of a particular protecting group will be determined generally by the conditions under which the tetramic acid thereof is formed and by the types of protecting groups used on the side chains of the other components to be used in synthesis. In a most preferred embodiment, the protecting groups are photoremovable and their removal is accomplished by exposing the surface or selected regions thereof to light (e.g., from a light source through a mask) or removable under neutral conditions. Such protecting groups and techniques are described in U.S. Pat. No. 5,148,854 and co-pending U.S. patent applications Ser. No. 07/624,120, filed Dec. 6, 1990, and 07/971,181, filed Nov. 2, 1992.

If the amine component comprises a beta-amino acid rather than an alpha-amino acid, a pentamic acid derivative is formed upon contact of the amine component with a β-keto ester and subsequent cyclization and cleavage:

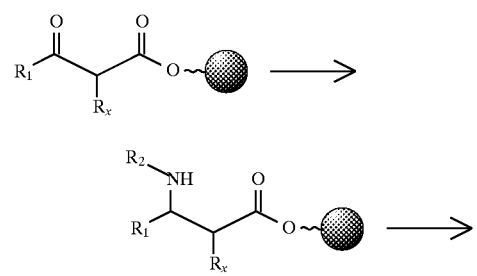

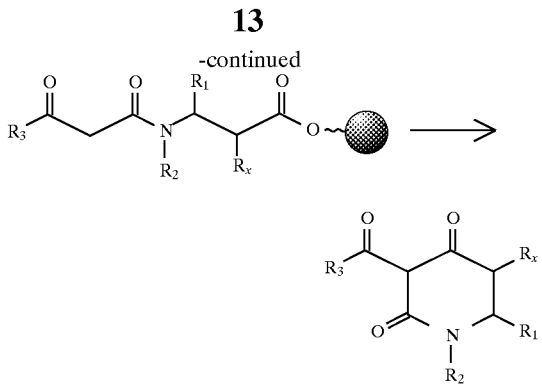

C. The β-keto ester equivalent

The amine component discussed above is contacted with a β-keto ester equivalent to yield a β-keto amide. Preferably, the β-keto ester equivalent will comprise an acyl Meldrum's acid, a lower alkyl ester of a β-keto carboxylic acid, or an acyl chloride of a β-keto carboxylic acid. Most preferably, the β-keto ester equivalent will comprise an acyl Meldrum's acid. Acyl Meldrum's acids can be readily prepared through the reaction of a carboxylic acid or acyl chloride with Meldrum's acid.

The β-keto ester equivalent can bear a wide variety of substitutents. For example, $R^3$ can be selected from the groups consisting of hydrogen, alkyl, aryl, heteroaryl, carboxyl, carboxyalkyl, carboxyaryl, and arylalkyl, each of which can be optionally substituted.

In a preferred embodiment, the amine component will comprise the limiting reagent and an excess of the β-keto ester_equivalent will be used. Typically, the ratio of amine component to β-keto ester_equivalent will range from about 1:1.1 to about 1:100, preferably from about 1:1 to about 1:10.

IV. The Method—Tetramic Acids

A. Immobilization of the Amine Component

As discussed above, the amine component will include a functionality that covalently binds the molecule to the solid support, e.g., activated carbonyl, acyl halide, ester, amide, or thioester, in addition to the amino group. The choice of functionality depends on the nature of the monomer and the type of solid support. Conditions for coupling through a wide variety of functional groups are known in the art. Preferably, Mukaiyama reagent is utilized to effect the coupling. Other preferred reagents useful for coupling the amine component to the solid support include DIC/DMAP and DIAD/PPh$_3$. Typically, between about 0.1 and about 0.5 equivalents of DMAP or between about 5–10 equivalents of DIC, based on resin loading, will be used. These solid phase synthesis procedures are well known in the art and further described, for example, by Stewart and Young, *Solid Phase Peptide Synthesis* (2nd Ed., Pierce Chemical Company, 1984).

Typically, the amine component is coupled via its carboxy terminus to the support. Preferably, a support having hydroxyl groups at the surface will be utilized. Suitable solid supports include TentaGel, ArgoGel, Merrifield resin and hydroxy-PAM resin (available from Advanced Chemtech). In a preferred embodiment, Merrifield resin, ArgoGel or a TentaGel hydroxy resin is used. Most preferably, a resin preloaded with amino acid esters is used.

The active sites of the surface and/or the amine component are optionally protected initially by protecting groups which may be acid-, base-, or photoremovable protecting groups as discussed above. Among a wide variety of protecting groups are materials such as Fmoc, BOC, t-butyl esters, t-butyl ethers, and the like. Various exemplary protecting groups are described in, for example, Atherton et al, *Solid Phase Peptide Synthesis,* IRL Press (1989), incorporated herein by reference and U.S. Pat. No. 5,148,854.

Each procedure for this reaction is preferably conducted in a single reaction medium employing an inert diluent or a mixture of inert diluents. The inert diluent employed in the reaction is not critical and suitable diluents include, by way of example only, acetonitrile, benzene, toluene, methylene chloride, chloroform, carbon tetrachloride, tetrahydrofuran and the like. Typically, the reactions will be conducted at a temperature of from about 0° C. to about 100° C. More preferably, a temperature of about ambient temperature will be used.

B. The Reductive Amination

According to some embodiments, the amino group of the bound first amino acid is alkylated. To effect this transformation, the bound first amino acid can be treated with conventional alkylating agents, such as $R^5CH_2X$, where X is bromine or iodine and where $R^5$ can be hydrogen or as discussed below; or with $R^5COOH$ to form the amide which can then be reduced, for example, with diborane to yield the alkylamine.

In a preferred embodiment, the bound first amino acid is treated with an aldehyde of formula $R^5CHO$ where $R^5$ is alkyl, aryl, heteroaryl, aralkyl, or heteroaralky or a ketone of formula $R^5 CO R^6$ where $R^5$ and $R^6$ are independently selected from the group consisting of alkyl, aryl, heteroaryl, aralkyl, or heteroaralky. (One of skill in the art will appreciate that any protecting groups present on the amine group of the bound first amino acid should be removed prior to the reductive amination reaction.) Preferably, the reductive amination is performed in the presence of a dehydrating reagent, as standard solid phase reaction conditions (aldehyde, sodium cyanoborohydride, 1% acetic acid in DMF) may result in over alkylation of the amino acid and yielded the corresponding N,N-dialkyl amino acid. Preferred dehydrating agents include molecular sieves, magnesium sulfate, sodium sulfate, trimethyl orthoformate, zinc chloride, and the like. More preferably, the dehydrating agent is in a form which can be easily washed away from the solid support or is even used as the solvent. Most preferably, the dehydrating agent comprises trimethylorthoformate.

Typically, an excess of both the aldehyde and the reducing agent is used. Preferably, at least 5 equivalents of aldehyde and/or at least 5 equivalents of reducing agent is used. More preferably, the alkylation is performed with about 10 equivalents or more of aldehyde and about 10 equivalents or more of reducing agent.

The reaction times and procedures will vary with the reactivity of the aldehyde. For example, with a short alkyl aldehyde with little steric hindrance (e.g., propanal or isovaleraldehyde), the bound first amino acid derivative is contacted with the aldehyde, preferably in the presence of the dehydrating agent. The reaction mixture is shaken or stirred for 30–60 minutes and then the reducing agent is added, preferably with additional dehydrating agent. For alkyl aldehydes with more steric hindrance (e.g., heptanal, t-butylacetaldehyde, and cyclohexane carboxaldehyde), the above procedure is followed. However, shortly after the reducing agent is added (e.g., 10 minutes), to the reaction is added a dilute solution of a protic solvent, preferably a 5% or less solution of a lower alkyl alcohol in trimethyl orthoformate, and more preferably about a 1% aqueous solution of methanol in trimethyl orthoformate. For aromatic and sterically hindered alkyl aldehydes (e.g., benzaldehyde, pivaldehyde, and 2-ethylbutanal), the procedure for short alkyl aldehydes is followed. However, a dilute solution of a weak acid, preferably a 5% or less solution of acetic acid in trimethyl orthoformate, more preferably about a 1% solution of acetic acid in trimethyl orthoformate, is added immediately after the addition of the reducing agent.

The reductive amination reaction can be followed by ninhydrin test or the Kaiser test. However, it should be noted that the preformed imines also give a red or brown color in the ninhydrin test and some are quite stable to hydrolysis therefore falsely indicating a completed reaction. Samples for the Kaiser test should be heated at least for 15 minutes.

C. Preparation of beta-keto acid equivalents

Beta-keto acid equivalents may be obtained via the acylation of Meldrum's acid. Typically, Meldrum's acid is treated with an acid chloride and DMAP in the presence of a base, such as pyridine. Alternatively, the acylation may be carried out by the in situ activation of a carboxylic acid with DCC and DMAP.

D. Treatment with the beta-keto acid equivalent

The resin-bound secondary amine is treated with 5–10 equivalents of the beta-keto acid equivalent in an apolar solvent, such as toluene. Typically, the reaction is conducted at an elevated temperature, for example, between about 30° C. and 100° C. Care must be taken to ensure that cyclative cleavage does not occur during this step. The reaction is usually complete within 4–6 hours. Excess reagents are removed and the resin is immediately subjected to the cyclization and cleavage protocol described below.

E. Cyclization and cleavage

The Diekmann intramolecular C-acylation (i.e., cyclization) and cleavage reactions can occur under either basic or acidic conditions. The preferred basic conditions involves treatment of the resin with one theoretical equivalent of a dilute base in a polar, protic solvent, such as 0.1M potassium hydroxide in methanol, diluted 1:1 with DCM. Alternatively, a dilute aqueous base in a polar, protic solvent, such as 0.8% aqueous sodium hydroxide in aqueous methanol can be employed, followed by treatment with a $H^+$ exchange resin. Preferred acidic conditions include the use of dilute aqueous acid in a polar protic solvent, such as 1% acetic acid in methanol or 1% TFA in methanol, or the use of $H^+$ exchange resin.

F. Results

A number of structurally diverse tetramic acids have been prepared using the described metholodolgy. As evidenced by the uniformly high yields that were obtained this approach is compatible with a variety of building blocks.

Significantly, it has been found that racemization was less than 5% with the optical purity of the amino acids being retained in the tetramic acids.

Preferred substituents at the 1, 3 and 5 positions of the tetramic acid ring which are prepared via the methods described herein from starting materials either known per se in the art or which can be prepared by art recognized methods are described above.

G. Assay

An assay has been developed which provides an estimate of the amount of tetramic acid present after cleavage. More specifically, it has been determined that several tetramic acids demonstrate an unique UV absorption at 280–290 nm with molar absorptivities in the range of $2-4 \times 10^4$. In addition, the complex of $Fe^{+3}$ and tetramic acids absorbs light at 470–480 nm with molar absorptivities in the range of $3-9 \times 10^2$. Preferably, the assay involves the dissolution of the compounds to be tested in a known volume of solvent. An aliquot is removed and diluted to yield a solution with 290 nm absorbance of 0.5–1.0 absorbance units. Beers law then allows for the calculation of the concentration of the subject compound.

V. Methods—Analogs

Other embodiments of the invention are drawn to the synthesis of analogs of tetramic acids, including thiotetronic acids, tetronic acids, pentonic acids, and thiopentonic acids and derivatives thereof. This class of compounds can be produced by using a hydroxyl component or a thiol component instead of the amine component.

More specifically, in a preferred embodiment, a hydroxyl component is immobilized on the solid support. According to some embodiments, the hydroxyl components can be produced via a β-keto acid which has been immobilized, preferably via its carboxy terminus. Reduction of the carbonyl group yields the corresponding β-hydroxy acid, i.e., the hydroxyl component. Esterification of the hydroxyl component with a beto-keto ester derivative followed by Diekmann cyclization and concomitant release from the support yields the tetronic or pentonic acid acid. Analogs of this basic ring structure can also be prepared using the components and basic protocols described above.

Typically the hydroxyl component will comprise a secondary hydroxyl having the formula:

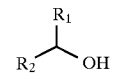

wherein $R^1$ and $R^2$ are independently selected from the groups consisting of hydrogen, alkyl, aryl, heteroaryl, carboxyl, carboxyalkyl, carboxyaryl, and arylalkyl. The hydroxyl component, if not commercially available, can be prepared by standard chemical procedures. In a preferred embodiment, the hydroxyl component will comprise a carboxylic acid or ester having a hydroxyl group at the beta carbon. Likewise, the thiol component will comprise the analogous structure wherein the hydroxyl group has been replaced with a thiol group.

A number of the hydroxy acids are commercially available. In addition, alpha-hydroxy acid analogs of the amino acids can be prepared from commercially available amino acids (or any hydroxy acid). For carboxylic acids having additional side chain functional groups, such as serine, threonine, and tyrosine, typically the side chain functional group will be protected (with a protecting group PG) prior to diazotization. Examples of suitable side chain protecting groups include, but are not limited to, t-butyl esters (for Glu and Asp); t-butyl ethers (for Ser, Thr, and Tyr); BOC (for Lys); and trityl amides (for Gln and Asn).

This synthetic route involves (1) diazotization with sodium nitrite in mild acid, such as acetic acid or citric acid; and (2) carboxy protection, preferably as the triisopropylsilyl group, and protection of the hydroxy group, typically with Fmoc-Cl; and carboxy deprotection. This reaction sequence is stereospecific and results in retention of the chirality of the carbon bearing the amino group (and thus, the carbon bearing the hydroxyl group). This latter multistep sequence can be performed without intermediate product isolation and purification. This reaction sequence will generally produce the desired hydroxy acid in 35–70% isolated overall yield.

The hydroxyl component may also be formed via binding a beta-keto ester equivalent to the solid support and reducing the ketone group via conventional means appreciated in the art.

If the hydroxyl component possesses reactive sites other than the amino group, it may be necessary to protect them during the synthesis. Suitable protecting groups include acid-labile, base-labile, photoremovable, or removable under neutral conditions. See, e.g., Green, *Protecting Groups in Organic Synthesis,* Wiley 1985, pp. 218–288, which is incorporated herein by reference. The choice of a particular protecting group will be determined generally by the conditions under which the tetramic acid thereof is formed and by the types of protecting groups used on the side chains of the other components to be used in synthesis. In a preferred embodiment, the protecting groups are photoremovable and their removal is accomplished by exposing the surface or selected regions thereof to light (e.g., from a light source through a mask) or removable under neutral conditions. Such protecting groups and techniques are described in U.S. Pat. No. 5,148,854 and co-pending U.S. patent application Ser. Nos. 07/624,120, filed Dec. 6, 1990, and 07/971,181, filed Nov. 2, 1992.

The immobilized β-keto acid, i.e., the precursor of the hydroxyl component can be prepared as shown below:

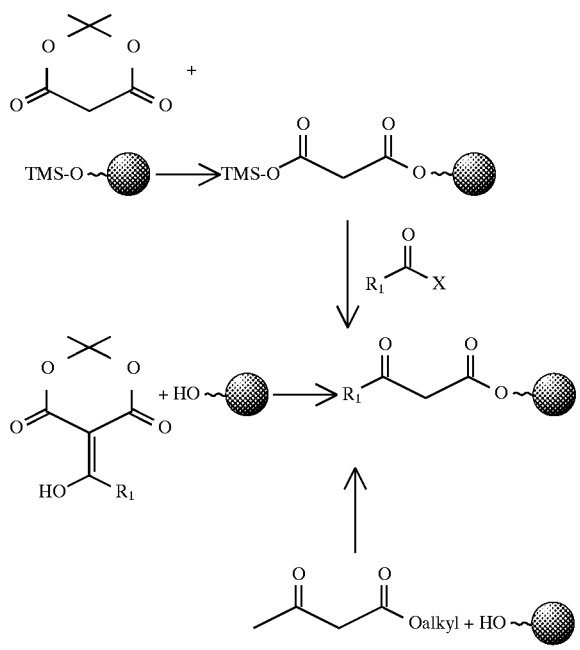

One of skill in the art will readily recognize that derivatives of the resulting beta keto ester can be produced by treatment of the compound with two equivalents of strong base, followed by an alkyl halide.

More specifically, Meldrum's acid can be contacted with a solid support bearing hydroxyl groups, followed by treatment with an acylating agent to yield the desired immobilized β-keto acid. Likewise, the immobilized β-keto acid can be produced through the treatment of a solid support bearing hydroxyl groups with an acylated derivative of Meldrum's acid or a lower alkyl ester of a beta-keto carboxylic acid.

VI. Method for Producing Large Synthetic Libraries

The above described synthetic methods can be incorporated into one or more reaction procedures in the stochastic methods described in International Patent Application Publication No. 93/06121 to prepare synthetic libraries of tetramic acids. This application is incorporated herein by reference in its entirety.

It is understood, however, that the term "single compound" as used herein includes different regio and stereoisomers of that compound. Also, the term "single compound" does not mean that only one copy of that compound is attached to each support. Rather, multiple copies of that compound can be included on the support.

Preferably, the library will contain at least about $10^2$ compounds, more preferably from about $10^2$ to about $10^{10}$ compounds and still more preferably from about $10^3$ to about $10^6$ compounds.

In another preferred aspect of this embodiment, each solid support is tagged with an identifier tag that can be easily decoded to report the compounds formed on the solid support. The tag can be directly attached either to the solid support or the tag can be included on the compound itself. In this latter embodiment, cleavage of the compound from the solid support will still permit identification of the compound. Each of these embodiments is disclosed in International Patent Application Publication No. WO 93/06121. Alternatively, a portion of the same compounds attached to a single support is cleaved and subjected to mass spectroscopy, nuclear magnetic resonance spectroscopy and/or other forms of direct structural analysis so as to identify the compound on the support.

Still another method for incorporating a tag with the solid support is disclosed in U.S. patent application Ser. No. 08/146,886 and entitled "METHOD OF SYNTHESIZING DIVERSE COLLECTIONS OF COMPOUNDS" which application is incorporated herein by reference in its entirety.

Additionally, libraries of compounds attached to solid supports can be used for a variety of additional uses as set forth in International Patent Application Publication No. WO 93/06121.

VII. Preparation of Derivatives and Analogs

The ring systems described above can be further manipulated. For example, 3-acyl-2,4-thiophenediones and 3-acyl-2,4-furandiones can be readily prepared. In addition, catalytic hydrogenation can also be used to reduce one or more of the carbonyl bonds.

Alkylidene derivatives can also be produced by the reaction of a tetramic acid ring having no substitution on the 5 position of the ring with an aldehyde. See, e.g., Harhash et al. (1973) *Ind. J. Chem.* 11:128–130.

The carbonyl group of the ring system is also amenable to further derivitization. For example, the tetramic acids can be reacted with hydroxyl amine to generate the corresponding 4-oximyl derivative. See, e.g., Diurno et al. (1992) *J. Med. Chem.* 35:2910–1912. Likewise, the tetramic acid ring can be treated with a substituted hydazine to provide a source of further diversity.

Additionally, if further functionality is present on the tetramic acid ring system, this functionality can be modified. For example, if one of the substituents is —$CH_2COOH$, then this acid functionality may be further reacted with a variety of amines, thiols, alcohols, and the like to produce amides, thioesters, esters, etc. Techniques for the further manipulation of a support-bound carboxyl group are known in the art and can be found in copending U.S. application Ser. Nos. 08/201,607, filed Feb. 25, 1994, and 08/179,741, filed Jan. 11, 1994, each of which is incorporated herein by reference.

Alternatively, if one of the substituents is an amino group, the corresponding tetramic acid could be derivatized with a variety of isocyanates, carboxylic acids, amino acids, and the like using techniques known in the art.

The above examples are illustrative; other transformations, such as alkylations, acylations, and the like, will be apparent to those skilled in the art.

EXAMPLES

The following examples are set forth to illustrate the claimed invention and are not to be construed as a limitation thereof.

Unless otherwise stated, all temperatures are in degrees Celsius. Also, in these examples, unless otherwise defined below, the abbreviations employed have their generally accepted meaning:

FMOC=fluorenylmethyl oxycarbonyl
$^1$H-nmr=proton nuclear magnetic resonance
HPLC=high performance liquid chromatography
mL=milliliter
mmol=millimol
NMP=N-methylpyrrolidone
TFA=trifluoroacetic acid
THF=tetrahydrofuran
μL=microliters General procedures: Unless otherwise noted, materials were obtained from commercial suppliers and used without further purification.

General Procedure for the Preparation of Acyl-Meldrum's Acids:

Method A: Acyl Chlorides. A solution of Meldrum's acid (50 mmol) and DMAP (100 mmol) in DCM (150 mL) was cooled under argon in an ice-salt bath to −5° C. A solution of the acid chloride (60 mmol) in DCM (50 mL) was added dropwise over 60 min, maintaining the temperature below 0° C. during the addition. The resulting solution was stirred at 0° C. for 60 min, then at room temperature for an additional 60 min. The reaction mixture was washed with 1M HCl (3×35 mL) and water (50 mL), dried over MgSO$_4$, and the solvent removed in vacuo. The residual solid was recrystallized from acetone to afford the product.
5-Benzoyl-2,2-dimethyl-1,3-dioxane-4,6-dione.
Method B: Carboxylic Acids. To a solution of the carboxylic acid (20 mmol), Meldrum's acid (20 mmol), and DMAP (40 mmol) in DCM (60 mL) at room temperature was added DCC (20 mmol). After stirring for 60 min, the precipitated dicyclohexylurea was removed by filtration and the filtrate washed with an ice-cold solution of 10% HCl (75 mL). The organic layer was dried over Na$_2$SO$_4$ and the solvent removed in vacuo. The residual solid was recrystallized from ethyl acetate/petroleum ether to afford the product.
5-(Phenylacetyl)-2,2-dimethyl-1,3-dioxane-4,6-dione.
5-Propionyl-2,2-dimethyl-1,3-dioxane-4,6-dione.

General Procedure for the Solid Phase Synthesis of 3-Acyl-2,4-pyrrolidinediones: Boc-Xaa-O-Resin (Merrifield, 250 mg, substitution 0.5–0.9 meq/g) was swollen in DCM and deprotected by treatment with a 25% TFA in DCM solution containing 1 mg/mL indole, once for 2 min and once for 30 min. After washing 5× with DCM, the resin was neutralized with a 10% TEA in DCM solution(2×) and washed 5× with DCM. Reductive alkylation. The resin was suspended in a 1:1 mixture of DCM/TMOF (3 mL), and acetic acid (30 mL) and the aldehyde (20 eq.) were added. After shaking for 30 min at room temperature, sodium cyanoborohydride (30 eq.) was added and shaking was continued for an additional 60 min. The resin was washed 3× with MeOH and 3× with DCM. Acylation. The resin was suspended in toluene (3 mL) and the acyl Meldrum's acid (6 eq.) was added. The mixture was heated at 65° C. for 6 hr. The resin was washed 3× with toluene and 3× with DCM. Cyclative cleavage. The resin was suspended in a 1:1 mixture of DCM/MeOH, and a solution of KOH in MeOH (0.1M, 1.0 eq.) was added. After shaking for 30 min the resin was removed by filtration and washed with MeOH/DCM. The filtrates were combined and the solvent removed in vacuo to afford the potassium salt of the 3-acyltetramic acid 7. The potassium salt was converted to the free acid by dissolving it in DCM, washing with 1M HCl, drying over Na$_2$SO$_4$, and removing the solvent in vacuo.

Examples of tetramic acids: The following lists representative examples of tetramic acids produced by the general procedures described above and isolated yields for these compounds.

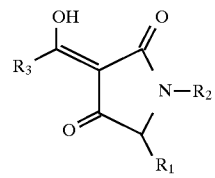

| Cpd | $R_1$ | $R_2$ | $R_3$ | Isolated Yield |
|---|---|---|---|---|
| 7a | (S)-PhCH$_2$ | n-Propyl | Ethyl | 69% |
| 7b | (S)—PhCH$_2$ | n-Propyl | Ph | 92% |
| 7c | (S)—PhCH$_2$ | n-Propyl | PhCH$_2$ | 51% |
| 7d | (S)—PhCH$_2$ | PhCH$_2$ | Ethyl | 74% |
| 7e | (S)—PhCH$_2$ | PhCH$_2$ | Ph | 92% |
| 7f | (R)—PhCH$_2$ | PhCH$_2$ | Ph | 76% |
| 7g | (S)—PhCH$_2$ | PhCH$_2$ | PhCH$_2$ | 66% |
| 7h | (S)—PhCH$_2$ | (C$_6$H$_{11}$)CH$_2$ | Ethyl | 73% |
| 7i | (S)—PhCH$_2$ | (C$_6$H$_{11}$)CH$_2$ | Ph | 80% |
| 7j | (S)—PhCH$_2$ | (C$_6$H$_{11}$)CH$_2$ | PhCH$_2$ | 77% |
| 7k | (S)-i-Propyl | n-Propyl | Ethyl | 64% |
| 7l | (S)-i-Propyl | n-Propyl | Ph | 64% |
| 7m | (S)-i-Propyl | n-Propyl | PhCH$_2$ | 68% |
| 7n | (S)-i-Propyl | PhCH$_2$ | Ethyl | 55% |
| 7o | (S)-i-Propyl | PhCH$_2$ | Ph | 61% |
| 7p | (S)-i-Propyl | PhCH$_2$ | PhCH$_2$ | 59% |
| 7q | (S)-i-Propyl | (C$_6$H$_{11}$)CH$_2$ | Ethyl | 43% |
| 7r | (S)-i-Propyl | (C$_6$H$_{11}$)CH$_2$ | Ph | 54% |
| 7s | (S)-i-Propyl | (C$_6$H$_{11}$)CH$_2$ | PhCH$_2$ | 53% |
| 7t | (S)-p-HOC$_6$H$_4$CH$_2$ | PhCH$_2$ | Ph | 67% |
| 7u | (S)-HOCH$_2$ | PhCH$_2$ | Ph | 51% |

Preparation of α-Hydroxy Acids from α-Amino Acids 5.1 Method A

To D-phenylalanine (2.00 g, 12.4 mmol) in water (20 mL), was added 3M HCl (20 mL, 60 mmol) and acetic acid (10 mL). The solution was cooled to 0° C., and an aqueous solution of sodium nitrite (3.92 g, 56.8 mmol, in 7.5 mL of water) was added dropwise over 10 minutes. The reaction was stirred for eight hours, then more sodium nitrite was added (3.92 g, 56.8 mmol, in 7.5 mL of water). After six hours, the solution was washed with ether (3×25 mL), and the combined organic layers were extracted with saturated sodium bicarbonate (3×30 mL). The bicarbonate washes were combined, acidified to pH 1 with concentrated HCl, and then extracted with ether (3×30 mL). The organic layers were combined, dried (magnesium sulfate), filtered, and then concentrated to afford 1.65 g of a white waxy solid (80%).

5.2 Preparation of (D)-O-nitroveratryloxy-methoxy-2-oxy-4-methylpentanoic Acid

The hydroxy acid prepared above was esterified using diazomethane, and to the resulting compound, methyl (D)-2-hydroxy-4-methyl valerate (1.0 g, 6.85 mmol) in 10 mL of methylene chloride was added Nvom chloride (2.69 g, 10.5 mmol) and diisopropylethyleneamine (DIEA, 1.8 mL). After 12 hours, the reaction mixture was diluted with methylene chloride (20 mL), washed with water (2×15 mL), and the organic layer dried (over $MgSO_4$). The product was purified by silica gel chromatography (4:1 petroleum ether:ethyl acetate) to afford 1.2 g of material (47%). The free acid was obtained in quantitative yield by hydrolysis with lithium hydroxide, as previously described. One could also prepare this compound, with possibly higher yield and shorter reaction time, using sodium hydride/THF instead of DIEA/dichloromethane.

5.3 Preparation of Side Chain Functionalized α-O-FMOC-Hydroxy Acids

To a solution of the hydroxy acid prepared above (with the side chain functionality protected, 1 mmol) in dry pyridine at 0° C. is added N-methylmorpholine (2.5 mmol) and triisopropylsilyl chloride (1.1 mmol). The solution was stirred for 15 minutes. To the reaction mixture is then added FMOC-Cl (1.1 mmol) and additional N-methylmorpholine. The reaction is stirred for 4–8 hours until complete. To the mixture is then added tetrabutylammonium fluoride (2.5 mmol). The reaction mixture is stirred for 15 minutes and quenched.

We claim:

1. A method of synthesizing compounds comprising tetramic acids, pentamic acids, and derivatives thereof, comprising the steps of:
   (a) on the surface of a solid support, providing an immobilized amine component;
   (b) contacting said immobilized amine component with a β-keto ester equivalent to yield a β-keto amide; and
   (c) treating the β-keto amide under conditions suitable for the cyclization and concomitant release of the compound from the solid support.

2. The method of claim 1, wherein the step of providing an immobilized amine component comprises the step of binding an amino acid to the support to form an immobilized amino component.

3. The method of claim 2, wherein the amino acid is an alpha amino acid and the compound synthesized by said method is a tetramic acid.

4. The method of claim 2, wherein the amino acid is a beta amino acid and the compound synthesized by said method is a pentamic acid.

5. The method of claim 1 or 2, wherein the amine component is alkylated.

6. The method of claim 1, wherein the solid support is a polymer bead.

7. The method of claim 1, wherein the β-keto ester equivalent is an acyl Meldrum's acid.

* * * * *